United States Patent
Zhong et al.

(10) Patent No.: US 12,012,519 B2
(45) Date of Patent: Jun. 18, 2024

(54) LIQUID-LIQUID PHASE SEPARATION DRIVEN PROTEIN-BASED UNDERWATER ADHESIVE COATINGS

(71) Applicant: ShanghaiTech University, Shanghai (CN)

(72) Inventors: Chao Zhong, Shanghai (CN); Mengkui Cui, Shanghai (CN)

(73) Assignee: ShanghaiTech University, Shanghai (CN)

( * ) Notice: Subject to any disclaimer, the term of this patent is extended or adjusted under 35 U.S.C. 154(b) by 803 days.

(21) Appl. No.: 17/169,581

(22) Filed: Feb. 8, 2021

(65) Prior Publication Data

US 2021/0155826 A1    May 27, 2021

Related U.S. Application Data

(63) Continuation of application No. PCT/CN2019/100159, filed on Aug. 12, 2019.

(51) Int. Cl.
| | |
|---|---|
| *C12N 15/62* | (2006.01) |
| *B82Y 30/00* | (2011.01) |
| *C07K 14/435* | (2006.01) |
| *C09D 189/00* | (2006.01) |

(52) U.S. Cl.
CPC .......... *C09D 189/00* (2013.01); *C07K 14/435* (2013.01); *C07K 2319/20* (2013.01)

(58) Field of Classification Search
CPC .. C09D 189/00; C07K 2319/20; C12N 15/62; B82Y 30/00; B82Y 40/00
See application file for complete search history.

(56) References Cited

U.S. PATENT DOCUMENTS 10,449,267 B2 * 10/2019 Lu .............................. C09J 5/00

FOREIGN PATENT DOCUMENTS

CN           107446052        * 12/2017

* cited by examiner

*Primary Examiner* — Maryam Monshipouri
(74) *Attorney, Agent, or Firm* — Richard Aron Osman

(57) ABSTRACT

Liquid-liquid phase separation (LLPS) driven protein-based underwater adhesive coatings are made from a dimeric protein comprising a marine adhesive protein (MAP) domain and a liquid-liquid phase separation-mediating low complexity (LC) domain.

20 Claims, 6 Drawing Sheets

Specification includes a Sequence Listing.

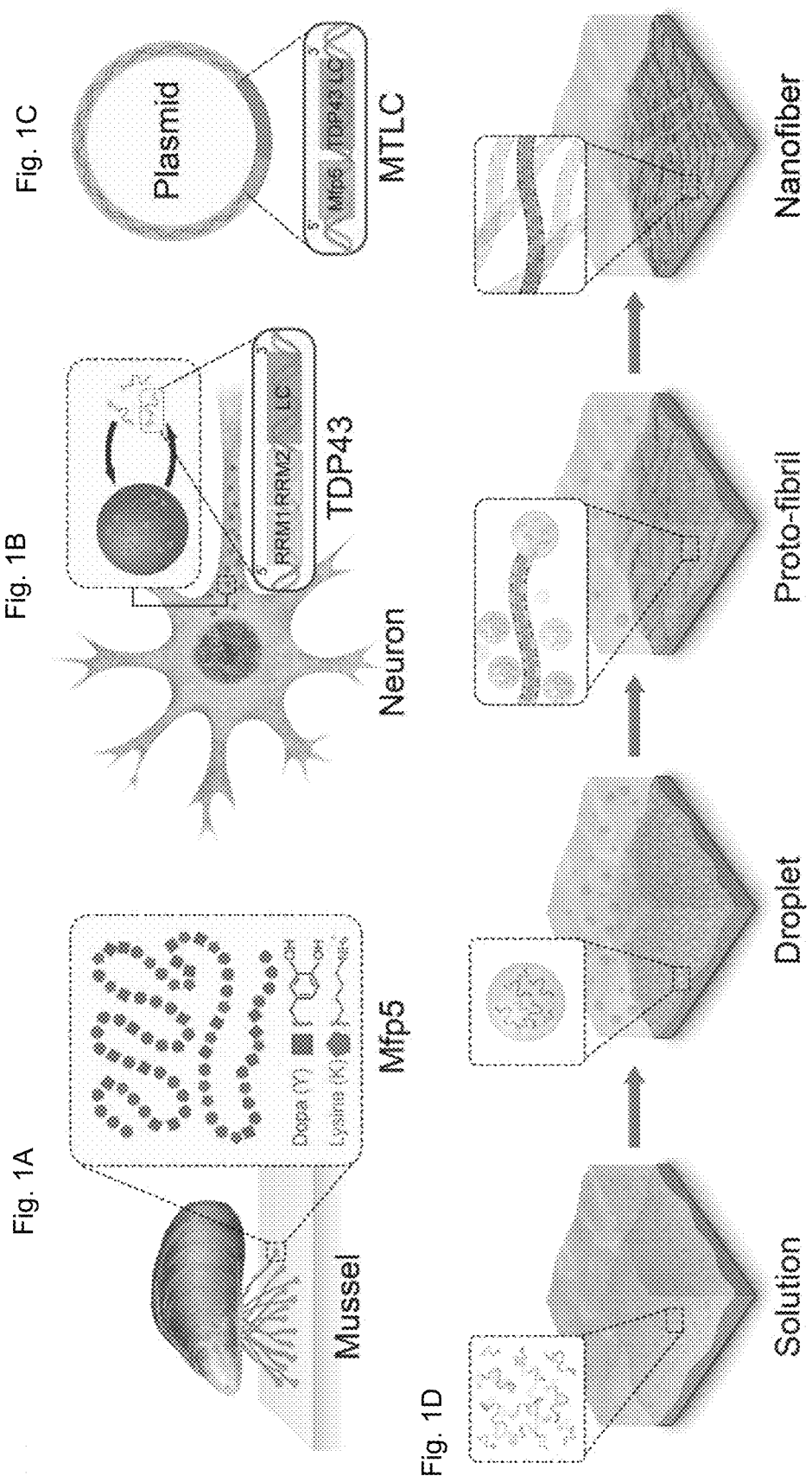

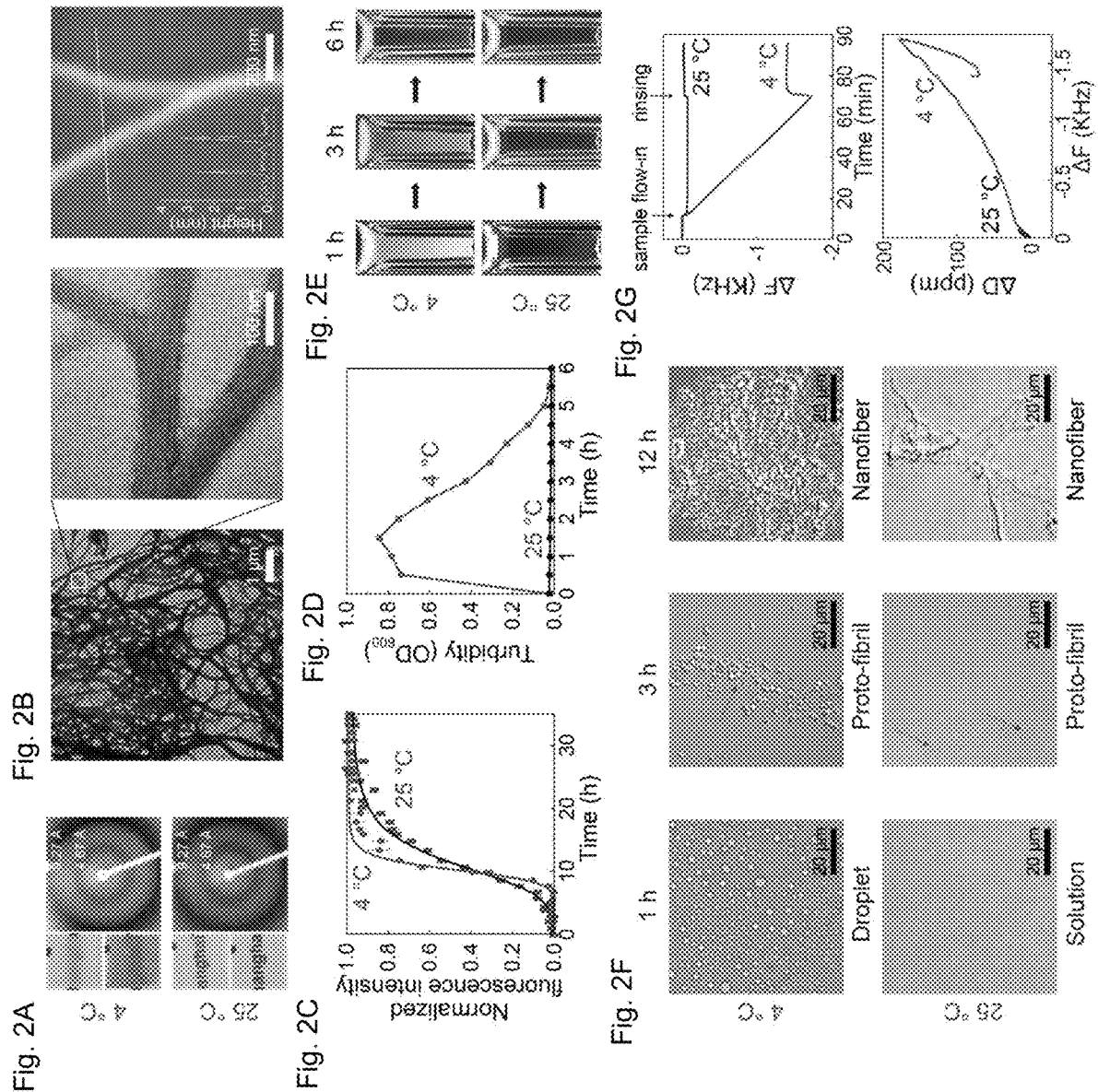

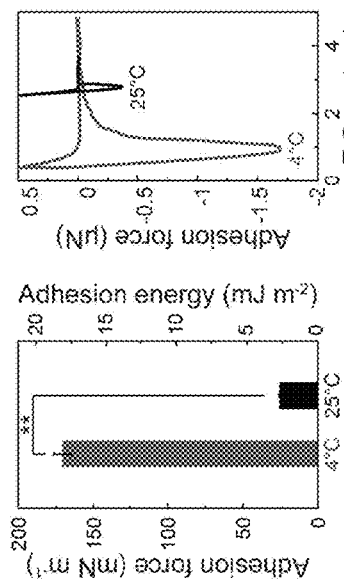
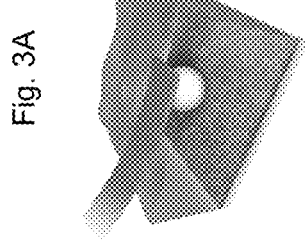
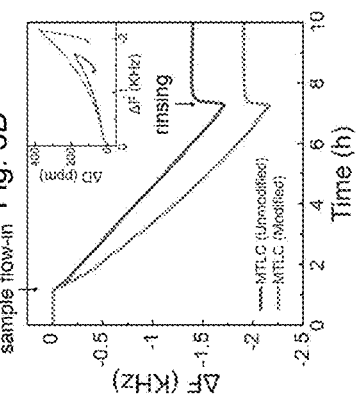
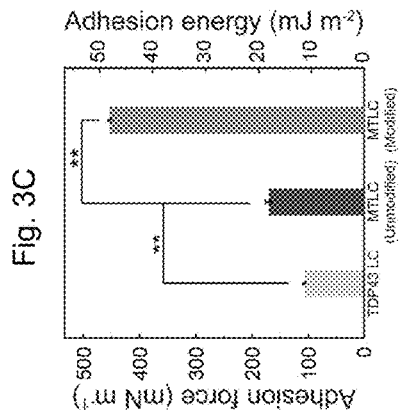
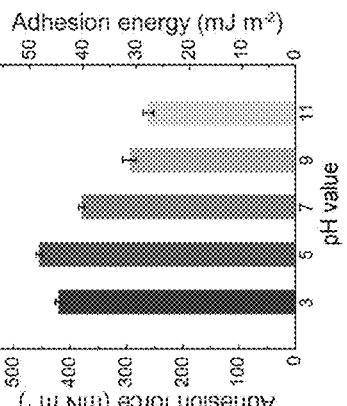
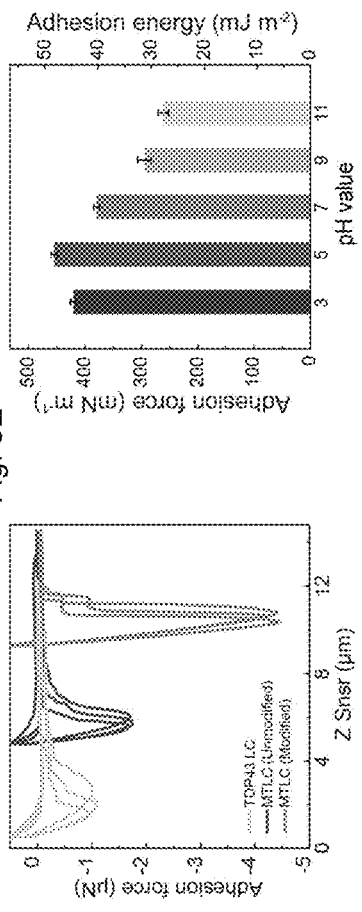

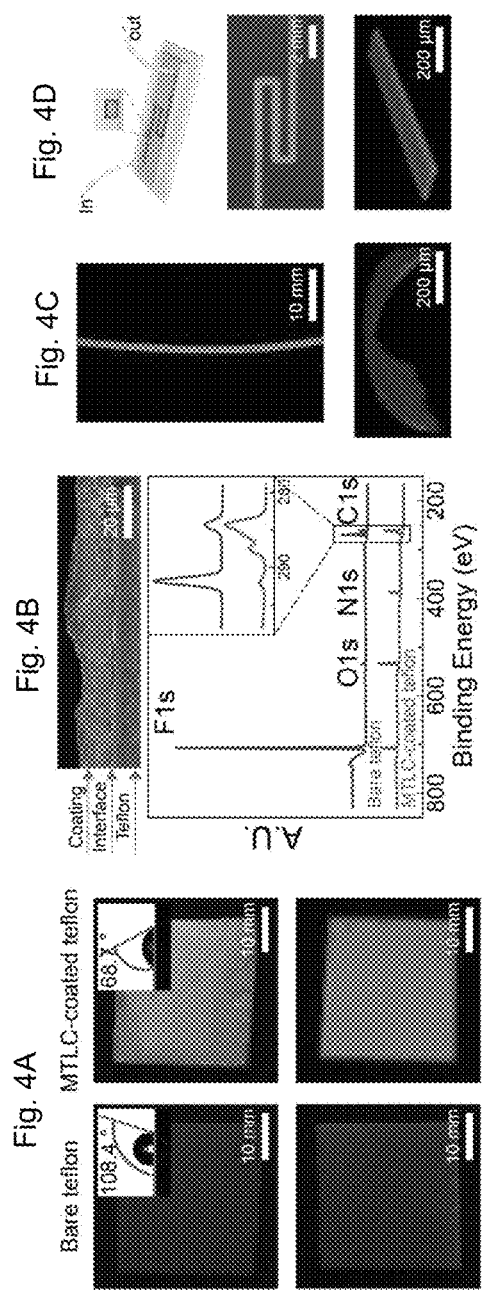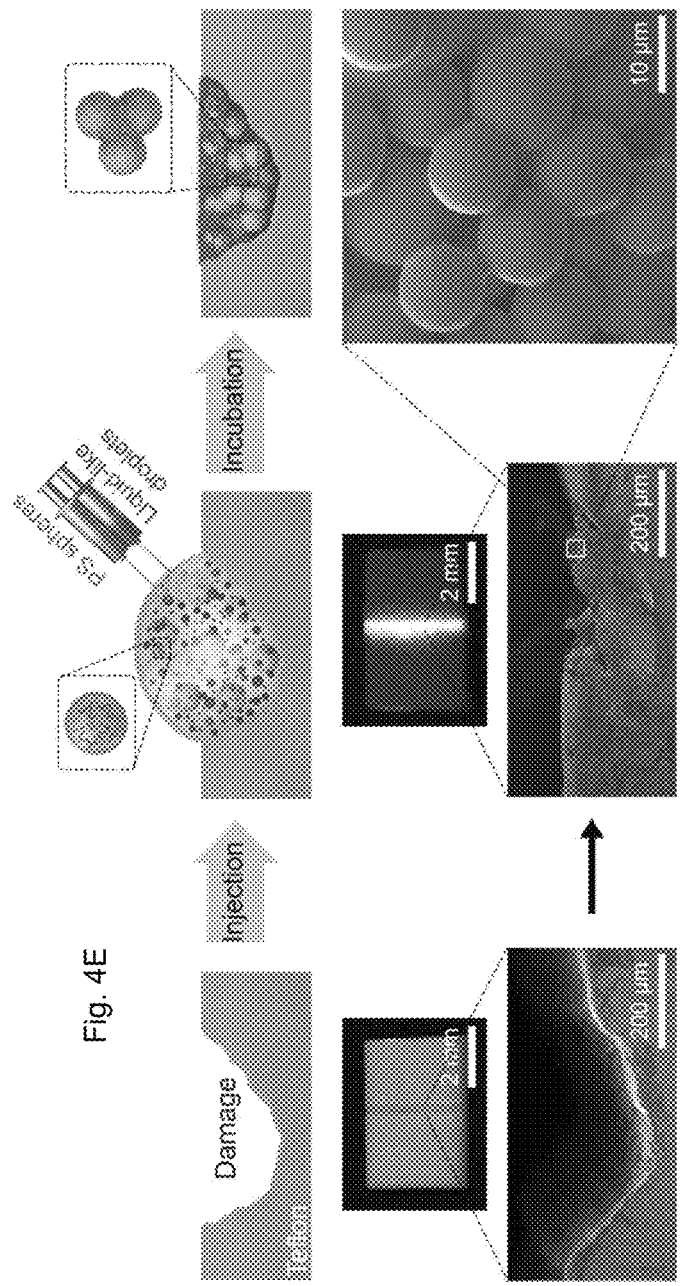

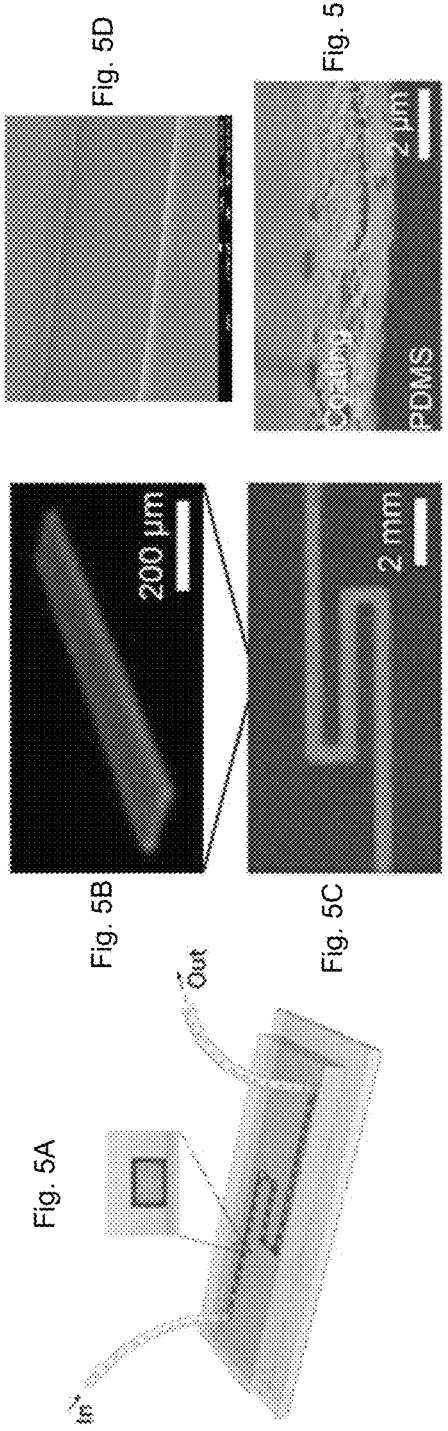
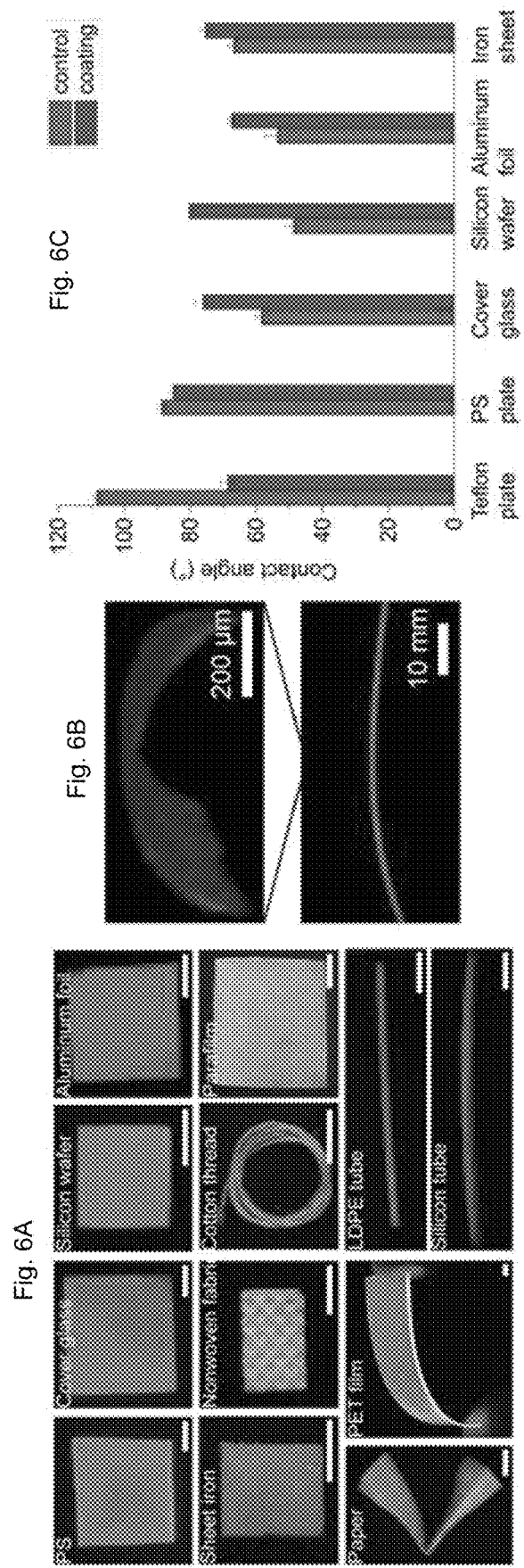

LIQUID-LIQUID PHASE SEPARATION DRIVEN PROTEIN-BASED UNDERWATER ADHESIVE COATINGS

INTRODUCTION

Liquid-liquid phase separations (LLPS), which can be promoted by low-complexity (LC) domains in proteins, are highly physiologically relevant with medical implications; for example, mutations which affect a protein's LLPS capacity can drive the pathogenesis of neurodegenerative diseases, such as amyotrophic lateral sclerosis (ALS) and ubiquitin-positive frontotemporal lobar degeneration (FTLD-U). Our research group explores bio-inspired underwater adhesives inspired by the anchoring plaques used by marine creatures like mussels, barnacles, and sandcastle worms. Seeking to develop ultra-strong underwater adhesive coatings, and taking inspiration from biophysical processes that are known to increase wetting, we explored the use of LLPS to improve the wetting properties and self-assembly of LC-domain-containing proteins as underwater adhesives. We demonstrate that an LLPS-driven mechanism promoted the wetting, adsorption, priming, and formation of dense and uniform amyloid nanofiber coatings on diverse substrates, including challenging materials like Teflon and difficult-to-access locations like the interior surfaces of microfluidic devices. Moreover, the coatings can be easily deposited on substrates over a wide range of pH values. Our LLPS-driven coatings have underwater adhesion energies far greater than the strongest ever reported protein-based underwater adhesives.

SUMMARY OF THE INVENTION

The invention provides methods and compositions for making liquid-liquid phase separation (LLPS) driven protein-based underwater adhesive coatings. In an aspect the invention provides a dimeric protein comprising a marine adhesive protein (MAP) domain and a liquid-liquid phase separation (LLPS) mediating low complexity (LC) domain.
In embodiments:
the domains are linked in a fusion protein;
the domains are linked through affinity tags on the domains;
the marine adhesive protein (MAP) comprises a polypeptide selected from:
a) mussel foot proteins (mfp5, mfp3, mfp3s);
b) barnacle proteins (cp19k, cp20k, and cp68k barnacle surface adhesive proteins); and
c) sandcastle worm adhesive proteins (Pc2 and Pc3);
the low complexity (LC) domain comprises a polypeptide selected from:
LC domain TAR DNA-binding protein 43 (TDP-43) (263-414);
RNA binding protein Fused in Sarcoma (FUS) (2-214);
Heterogeneous nuclear ribonucleoprotein A1 (hnRNPA1) (186-320);
Heterogeneous nuclear ribonucleoprotein A2 (hnRNPA2) (181-341);
Cytotoxic granule-associated RNA binding protein TIA1 (280-375);
Cytoplasmic polyadenylation element binding protein 2 (CPEB2) (2-137);
Fragile X mental retardation protein (FMRP) (466-632);
Cold inducible RNA binding protein (CIRBP) (1-172);
RNA binding motif (RNP1, RRM) protein 3 (RBM3) (1-157); and
Yeast Sup35 (2-134); and/or
the dimeric protein is selected from specific examples, including: GFP-FUS LC-mfp5, mfp5-FUS LC, mfp3-TDP-43 LC, mCherry-FUS LC-mfp3 and Spytag-FUS LC:mfp5-spycatcher.

In an aspect the invention provides an amyloid nanofiber coating comprising a subject dimeric protein, especially underwater, and especially wherein the coating is micropatterned on a substrate. In embodiments the coating provides underwater adhesion energy at least double, and typically 2-3 times, that of the corresponding MAP coating, typically greater than 30 or 40 mJ m$^{-2}$, such as in the range of 30-50 or 40-50 mJ m$^{-2}$.

In an aspect the invention provides a substrate comprising a subject coating.

In embodiments the substrate is selected from metal, polymer and inorganic substrates, flexible and interior substrate surfaces, such as microfluidic channels and microtubules.

In an aspect the invention provides a method of making an amyloid nanofiber coating on a substrate comprising: incubating a subject dimeric protein under conditions wherein a LLPS induced amyloid nanofiber coating comprising the dimeric protein forms on the substrate.

In embodiments:
the method is operated or operable over a range of pH conditions that is pH3-11.
the substrate is selected from metal, polymer and inorganic substrates, flexible and interior substrate surfaces, such as microfluidic channels and microtubules.
the coating is micropatterned on the substrate, such as by mask-assisted patterning or soft lithography (such as microtransfer molding or replica molding).

The invention includes all combinations of recited particular embodiments as if each combination had been laboriously recited.

BRIEF DESCRIPTION OF THE DRAWINGS

FIGS. 1A-D. A combinatorial and modular protein domain strategy for engineering liquid-liquid phase separation-induced self-assembling underwater adhesives. (A) Schematic of the adhesive protein mfp5 that functions in the adhesion plaques of marine mussels. Mfp5, a mussel adhesion foot protein rich in lysine and Dopa residues, displays a random coil structure in solution and is essential for the interfacial underwater adhesion of mussels. (B) Schematic of the human TAR DNA-binding protein 43 (TDP-43), which along with specific RNAs, forms TDP-43 ribonucleoprotein (RNP) granules that mediate cellular processes in neuron cells. TDP-43 contains both RNA recognition motifs and a low-complexity domain, which is an intrinsically disordered domain enriched in glycine and uncharged polar amino acid residues that can contributes to the self-assembly of RNP granules that is driven by a process termed liquid-liquid phase separation (LLPS). (C) The modular genetic design of adhesive proteins is enabled by rationally fusing sequences encoding the protein domains shown in A and B to form a His-tagged mfp5-TDP-43 LC ("MTLC") fusion protein. (D) MTLC fusion protein monomers in solution can assemble into condensed liquid-like droplets driven by LLPS (left). The liquid-like droplets tend to spread over and adsorb on surfaces, facilitating a priming process for the MTLC coating (middle left). The liquid-like droplets are locally enriched near the substrate surface, and these droplets have high concentrations of protein monomers, thus promoting formation of proto-fibrils on the substrate (middle right). Additional monomers can then aggregate on these surface-localized proto-fibrils, eventually forming amyloid nanofiber coatings on the surface. The MTLC nanofiber coatings exhibit strong underwater adhesion owing to their high surface area and the adhesive properties of the MTLC mfp5 domains, which are exposed at the surface of the nanofibers, external to the amyloid core.

FIGS. 2A-G. Morphological and structural characterization of LLPS-induced MTLC adhesive coatings. (A) Photographs of adhesive coatings (top left) produced by incubating MTLC monomer solutions at 4° C. and 25° C. and staining of the corresponding samples with Congo Red (lower left). X-ray fiber diffraction pattern (right) of mfp5-TDP-43 LC nanofibers of two samples showed a typical diffraction pattern of cross-β spine of amyloid nanofibers in which the meridional reflection ($d_2$) is ~4.67 Å (corresponding to the spacing between β-strands within each layer of (3-sheets in the fibril) and the equatorial reflection ($d_1$) is ~9.27 Å (corresponding to the inter-sheet packing distances between each layer of (3-sheets in the fibril). (B) Morphological characterization of the hierarchical structure of MTLC coatings formed at 4° C. MTLC coatings were dense nanofiber meshes (TEM image, left) formed from nanofiber bundles that assemble via the lateral stacking of amyloid nanofibers (TEM image, middle). These nanofibers are about 3 nanometers in diameter (AFM image, right). (C) ThT fluorescence curve of MTLC in solutions incubated at 4° C. and 25° C. A ThT fluorescence assay was applied to monitor and quantify the kinetics of amyloid nanofiber formation. (D) Turbidity-time curve of MTLC in solution incubated at 4° C. and 25° C.; measured at $OD_{600}$. (E) Photographs of MTLC solutions incubated at 4° C. and 25° C. taken at different time intervals. (F) Differential interference contrast (DIC) microscopy images of phase-separation induced assembly of MTLC protein monomers adsorbed on a glass surface at 4° C. and 25° C. assessed after 1 h, 3 h, and 12 h of incubation. LLPS-driven formation of liquid-like droplets during the first 6 h, followed by the appearance of proto-fibrils in the vicinity of the liquid-like droplets. MTLC monomers then aggregate on the proto-fibrils, eventually producing dense MTLC nanofiber coatings. (G) Frequency change comparison in QCM-D experiments showing the different adsorption capacities of MTLC to a gold surface at 4° C. and 25° C. (top). Plots of ΔD vs ΔF (bottom) corresponding to the curve shown at the top. The ΔD/ΔF value indicates the stiffness of the coatings: higher ΔD/ΔF values suggest softer materials. THT and turbidity data shows means±s.e.m. of three replicate samples.

FIGS. 3A-E. Underwater adhesion performance of adhesive coatings. (A) Schematic of a colloidal AFM probe used to measure the asymmetric adhesion of adhesive coatings on smooth mica surfaces. (B) Comparison of adhesion forces (normalized force (F/R) and adhesion energies ($F_{ad}$=F/3πR)) for MTLC coatings produced at 4° C. and 25° C. (measured with a gold probe tip, R=10 μm). Representative adhesion force-distance curves in the right panel were collected on one spot of the coated mica surface using the single force mode (gold probe tip). (C) Comparison of adhesion forces and adhesion energies for the TDP-43 LC domain (control), unmodified MTLC, and DOPA-modified. MTLC coatings produced at 4° C. (gold probe tip) (top) and representative adhesion force-distance curves of the control TDP-43 LC, unmodified MTLC, and DOPA-modified MTLC coatings (bottom); the curves correspond to three random spots of the coated mica surface (single force mode; gold probe tip). (D) Frequency change comparison in QCM-D experiments showing the different adsorption capacities of unmodified MTLC and DOPA-modified MTLC coatings for a gold surface at 4° C. Plots of ΔD vs ΔF (inserted) corresponding to the frequency change curve. (E) Adhesion forces and adhesion energies for DOPA-modified MTLC coatings produced at a range of pH values (3-11) at 4° C. measured with a gold probe tip. For each comparison in B, C. and E, n=25 (5 spots per mica plate, with each spot sampled 5 times using single three mode). In B and D, the adhesion force curves are plotted as force-displacement curves: the x axis, ZSnsr (Z sensor), represents the displacement between the sample surface and the resting position of the cantilever (rather than the actual distance between the sample surface and the AFM tip).

FIGS. 4A-E. Applications of liquid-liquid phase separation induced MTLC adhesive coatings. (A) Digital camera images of uncoated polytetrafluoroethylene (TEFLON, "Teflon") (top left) and Teflon coated with phase separation-induced MTLC adhesives (top right) and red QDs adsorption on uncoated Teflon (bottom left) and LLPS-induced MTLC coated Teflon (bottom right) with inset data from the water contact angle analysis. Images were taken under UV light (254 nm). (B) SEM sectional image of a continuous layer of LLPS-induced MTLC adhesive coating formed on Teflon (top) and corresponding X-ray photoelectron spectroscopy (XPS) showing the distinctive element signals representative of N, O, and C (from protein structures) in the coated Teflon substrate, in contrast with the dominant F and C signals shown in the bare Teflon. (C) UV-illuminated photograph (top), and 3D confocal micrograph (bottom) of a Teflon pipe, showing red QDs adsorbed on the interior walls of the MTLC-coated pipe. (D) Schematic (top), UV-illuminated photograph (middle), and 3D confocal micrograph (bottom) of a microfluidic device with an MTLC-coated channel that was post-treated with red QDs. (E) Schematic illustration showing the repair of damage (scratch) on a Teflon substrate. We co-injected purified MTLC monomers in solution with non-sticky fluorescent spherical polystyrene (PS) micro-spheres around the damage site. Upon incubation at 4° C. for 12 hours, an LLPS-induced MTLC coating formed on the substrate and on the surface of the PS micro-spheres, acting as a glue to aggregate the micro-spheres to each other and with the substrate surface, thereby retaining them in place and thus filling the damage site (right). (E) Photograph (top) and SEM (bottom) images showing the damaged Teflon substrates before and after repair using LLPS-induced coatings. Photograph of the repaired sample taken under UV light (254 nm). A zoomed-in SEM image clearly showing that the micro-spheres were piled up and glued together in the damage site.

FIGS. 5A-E. (A) Schematic illustration showing the fluidic device made of PDMS covered on a glass slide. (B) 3D images taken by a confocal fluorescent microscopy. (C) In situ photograph taken under UV light. (D) SEM image and (E) SEM sectional image showing the inside walls of channel were coated with protein.

FIGS. 6A-C. (A) Digital images of red ODs assembled on MTLC coated surfaces. (B) 3D image of micro PE tube. Red QDs assembled on MTLC coated inside wall. (C) Water contact angle measurement of various surfaces with/without MTLC coatings.

DESCRIPTION OF PARTICULAR EMBODIMENTS OF THE INVENTION

Figure 7C:
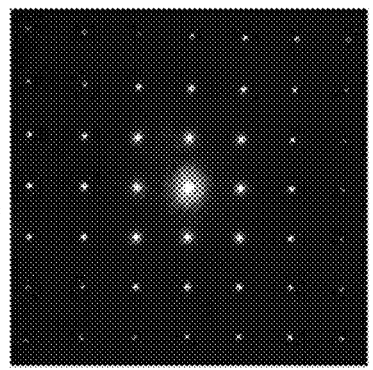
FIGS. 7A-C. (A) QDs assembled on lithography patterns mediated by specific mask plates. (B) QDs assembled on soft lithography patterns. (C) Micro-scale pattern displays an orderly light spot under green laser which indicates long range ordered pattern achieved.

The embodiments and examples herein are provided by way of illustration only and not by way of limitation. Those skilled in the art will readily recognize a variety of noncritical parameters that could be changed or modified to yield essentially similar results.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention provides methods and compositions for making liquid-liquid phase separation (LLPS) driven protein-based underwater adhesive coatings. In an aspect the invention provides a fusion protein comprising a marine adhesive protein (MAP) domain and a liquid-liquid phase separation (LLPS) mediating low complexity (LC) domain.

MAPs are a well-known and well-studied class of proteins (e.g. Wilker et al, Curr Opin Chem Biol. 2010 April; 14(2):276-83), including recombinant forms modified for functional properties, e.g. Yang et al. Biofouling. 2013; 29(5):483-90. In embodiments the MAP may be truncated, so long as functional amyloid nanofiber formation and adhesive properties are retained.

Liquid-liquid phase separation (LLPS) mediating low complexity (LC) domains are a well-known and well-studied class of proteins domains, with characterized structure-activity-relationships, e.g. Martin et al. Biochemistry. 2018 May 1; 57(17):2478-248; Kato et al., Cell, 2012, 149(4): 753-767; etc. In embodiments the LC may be truncated, so long as LLPS mediation functionality is retained.

The MAP and LC domains maybe linked domains are linked in a fusion protein or through affinity tags on the domains, which non-covalent, such as HA, myc, FLAG or His6 tags, or covalent, such as spytag, snooptag, isopeptag or dogtag.

Table A. Exemplary Truncated Functional LLPS-Mediating LC Domains

TAR DNA-binding protein 43 (TDP-43) (263-414)

(SEQ ID NO: 01)
KHNSNRQLERSGRFGGNPGGFGNQGGFGNSRGGGAGLGNNQGSNMGGGMN

FGAFSINPAMMAAAQAALQSSWGMMGMLASQQNQSGPSGNNQNQGNMQRE

PNQAFGSGNNSYSGSNSGAAIGWGSASNAGSGSGFNGGFGSSMDSKSSGW

GM

RNA binding protein Fused in Sarcoma (FUS) (2-214)

(SEQ ID NO: 02)
ASNDYTQQATQSYGAYPTQPGQGYSQQSSQPYGQQSYSGYSQSTDTSGYG

QSSYSSYGQSQNTGYGTQSTPQGYGSTGGYGSSQSSQSSYGQQSSYPGYG

QQPAPSSTSGSYGSSSQSSSYGQPQSGSYSQQPSYGGQQQSYGQQQSYNP

PQGYGQQNQYNSSSGGGGGGGGGGGNYGQDQSSMSSGGGSGGGYGNQDQSG

GGGSGGYGQQDRG

Heterogeneous nuclear ribonucleoprotein A1 (hnRNPA1) (186-320)

(SEQ ID NO: 03)
MASASSSQRGRSGSGNFGGGRGGGFGGNDNFGRGGNFSGRGGFGGSRGGG

GYGGSGDGYNGFGNDGSNFGGGGSYNDFGNYNNQSSNFGPMKGGNFGGRS

SGPYGGGGQYFAKPRNQGGYGGSSSSSSYGSGRRF

Heterogeneous nuclear ribonucleoprotein A2 (hnRNPA2) (181-341)

(SEQ ID NO: 04)
MQEVQSSRSGRGGNFGFGDSRGGGGNFGPGPGSNFRGGSDGYGSGRGFGD

GYNGYGGGPGGGNFGGSPGYGGGRGGYGGGGPGYGNQGGGYGGGYDNYGG

GNYGSGNYNDFGNYNQQPSNYGPMKSGNFGGSRNMGGPYGGGNYGPGGSG

GSGGYGGRSRY

Cytotoxic granule-associated RNA binding protein TIA1 (280-375)

(SEQ ID NO: 051)
INPVQQQNQIGYPQPYGQWGQWYGNAQQIGQYMPNGWQVPAYGMYGQAWN

QQGFNQTQSSAPWMGPNYGVQPPQGQNGSMLPNQPSGYRVAGYETQ

Cytoplasmic polyadenylation element binding protein 2 (CPEB2) (2-137)

(SEQ ID NO: 06)
PPPSPDSENGFYPGLPSSMNPAFFPSFSPVSPHGCTGLSVPTSGGGGGF

GGPFSATAVPPPPPPAMNIPQQQPPPPAAPQQPQSRRSPVSPQLQQQHQA

AAAAFLQQRNSYNHHQPLLKQSPWSNHQSSGWGTGSM

Fragile X mental retardation protein (FMRP) (466-632)

(SEQ ID NO: 07)
GQGMGRGSRPYRNRGHGRRGPGYTSGTNSEASNASETESDHRDELSDWSL

APTEEERESFLRRGDGRRRGGGGRGQGGRGRGGGFKGNDDHSRTDNRPRN

PREAKGRTTDGSLQIRVDCNNERSVHTKTLQNTSSEGSRLRTGKDRNQKK

EKPDSVDGQQPLVNGVP

Cold inducible RNA binding protein (CIRBP) (1-172)

(SEQ ID NO: 08)
MASDEGKLFVGGLSFDTNEQSLEQVFSKYGQISEVVVVKDRETQRSRGFG

FVTFENIDDAKDAMMAMNGKSVDGRQIRVDQAGKSSDNRSRGYRGGSAGG

RGFFRGGRGRGRGFSRGGGDRGYGGNRFESRSGGYGGSRDYYSSRSQSGG

YSDRSSGGSYRDSYDSYATHNE

RNA binding motif (RNP1, RRM) protein 3 (RBM3) (1-157)

(SEQ ID NO: 09)
MSSEEGKLFVGGLNFNTDEQALEDHFSSFGPISEVVVVKDRETQRSRGFG

FITFTNPEHASVAMRAMNGESLDGRQIRVDHAGKSARGTRGGGFGAHGRG

RSYSRGGGDQGYGSGRYYDSRPGGYGYGYGRSRDYNGRNQGGYDRYSGGN

YRDNYDN

Yeast Sup35 (2-134)

(SEQ ID NO: 10)
SDSNQGNNQQNYQQYSQNGNQQQGNNRYQGYQAYNAQAQPAGGYYQNYQG

YSGYQQGGYQQYNPDAGYQQQYNPQGGYQQYNPQGGYQQQFNPQGGRGNY

KNFNYNNSLQGYQAGFQPQSQGMSLNDFQKQQKQ

In this specific embodiment we designed a fusion protein comprising a full length adhesion foot protein from marine mussels (mfp5), the LC domain of the human TAR DNA-binding protein 43 (TDP-43), and an N-terminal His-tag to facilitate purification (FIG. 1A-C). mfp5 is a very 'sticky' protein rich in lysine and post-translationally modified tyrosine residues (L-3,4-dihydroxyphenylalanine; DOPA) that are essential for the interfacial interactions that facilitate the underwater adhesion of mussels (FIG. 1A). Human TDP-43, an amyloid protein comprised of two RNA recognition motifs and an LC domain (FIG. 1B), is known to form LLPS-driven ribonucleoprotein (RNP) granules that mediate cellular processes in neuron cells.

We anticipated (i) that our engineered mfp5-TDP-43 LC (MTLC) fusion protein monomers would form into condensed liquid-like droplets driven by LLPS, (ii) that the liquid-like droplets would tend to spread over and adsorb on substrate surfaces to facilitate a priming process for the MTLC coating, (iii) that the local enrichment of the MTLC in the droplets would promote the self-assembly of amyloid condensates at the surface, and (iv) that additional MTLC monomers would then aggregate on these surface-localized structures, driving the eventual formation of thick amyloid nanofiber coatings on the substrate (FIG. 1D). We also anticipated that the MTLC nanofiber coatings should exhibit very strong underwater adhesion, owing to their high surface area and the adhesive residues present on the mfp5 domains, which would be exposed at the surface of the nanofibers, external to the amyloid core.

In our initial attempts to apply purified MTLC monomers as adhesive coatings we observed a striking temperature-dependent phenomenon. Specifically, when incubated at 4° C., the MTLC fusion protein monomers formed a dense and uniform coating on a glass substrate. In contrast, when incubated at 25° C., only very sparse and inhomogeneous depositions were formed on the glass slide (FIG. 2A). Further, staining with the amyloid-specific dye Congo red revealed intense and uniform signals for the MTLC coating formed at 4° C., whereas the coating formed at 25° C. had a much weaker staining signal. TEM and AFM analysis confirmed that the MTLC coating materials formed at 4° C. were nanofiber mesh structures comprised of hierarchically arranged nanofibers (FIG. 2B). Further confirming the amyloid nature of the coatings, x-ray fiber diffraction analysis showed typical diffraction patterns for the cross-0 spine structures of amyloid nanofibres. It is important to note that although the depositions formed at 25° C. were very sparse, TEM and AFM revealed that these materials were also assembled as amyloid nanofibers.

Intrigued by the observation that incubation of MTLC monomers at 25° C. produced amyloid nanofibers but formed only sparse depositions on the glass substrate, we conducted an amyloid-specific dye assay (Thioflavin T, ThT) to monitor the amyloid assembly process over time at low (4° C.) and high (25° C.) temperatures (FIG. 2C). These assays revealed two distinct trends. First, whereas the high temperature samples exhibited amyloid assembly that started soon after the start of incubation, the low temperature samples had a much longer lag time prior to initiate amyloid assembly. Second, it took about 24 hours for the MTLC monomers of the high temperature samples to complete their assembly into amyloid nanofibers. In contrast, the amyloid assembly process for low temperature samples was completed within a much shorter time window (~10 h).

The extreme differences that we observed in the thickness and uniformity of coverage of the coatings formed at low vs. high temperature, and our findings that the temperature difference altered, but did not prevent, the amyloid assembly of MTLC monomers collectively suggest a kinetically trapped state in the low temperature samples during which MTLC monomers form liquid phase condensates in a process driven by LLPS. A hallmark feature of LLPS is high turbidity of solutions. We here conducted turbidimetry based on optical density measurements at 600 nm for a purified MTLC monomer solution over a 6 hour incubation timecourse at 4° C. and 25° C. and observed that, whereas the turbidity of the 4° samples rose from a very low level, subsequently rose sharply to quickly reach a plateau that lasted for around 2 hours, and then gradually declined, the turbidity of the 25° samples rose slightly but then sharply decreased without exhibiting any plateau (FIG. 2D).

We believe that the high turbidity plateau of the 4° C. samples delineates the aforementioned kinetically trapped state during which the liquid phase condensates are formed. Subsequent macro- and micro-scale observations of the low and high temperature samples collected at different time points further supported this hypothesis. Photographs of the low temperature MTLC incubation process showed that the low-temperature sample solutions became cloudy within several minutes, remained cloudy for 4-5 hours, and then became clear by hour 6, a point by which the amyloid nanofiber assembly process has already begun (FIG. 2E). Consistently, light microscopy showed that liquid-like droplets formed in the low temperature MTLC samples within 1 hour; no droplets formed at any point for the high temperature MTLC samples (FIG. 2F, FIG. S6). Fascinatingly, in the period of time between the initial deposition of these liquid-like droplets and eventual amyloid nanofiber formation in the low temperature MTLC samples, we observed that intermediate "proto-fibrils" formed in the immediate vicinity of the initially absorbed liquid-like droplets. Testing the LC domain-mediated LLPS process under a variety of experimental conditions by monitoring solution turbidity showed that temperature, ionic strength, and solution pH all affected the LLPS-driven formation of liquid-like droplets, but temperature appeared to exert the largest influence (FIG. S8). More specifically, lower temperature, lower ionic strength, and higher pH values all promoted phase separation of the MTLC monomers.

We next applied Quartz Crystal Microbalance with Dissipation monitoring (QCM-D) experiments to examine the different adsorption capacities of MTLC on a gold surface at 4° C. and 25° C. (FIG. 2G). The adsorption capacity of the MTLC solution at the low temperature was significantly higher than at the high temperature. Additionally, the large value of the acoustic ratio (ΔD/ΔF) observed for the low temperature solution was indicative of the presence of soft materials adsorbed on the gold surface. These results highlight the significant role of LLPS-driven liquid-like condensates in the formation of dense and uniform amyloid nanofiber coatings at substrate surfaces at low temperature: as liquid-like droplets, such condensates have low surface energy that effectively lowers the energy barrier required for surface wetting and subsequent adsorption.

To directly measure the underwater adhesion performance of MTLCs, we used a colloidal probe technique based on AFM that assesses the asymmetric adhesion of nanomaterials that are initially bound to clean and smooth mica in an aqueous buffer (FIG. 3A). We initially examined how the differences in coating density and uniformity between the low and high temperature MTLC coatings affected adhesive strength. The low-temperature MTLC coatings exhibited dramatically and significantly stronger adhesion than the high-temperature coatings (FIG. 3B). Indeed, the adhesive performance of the low-temperature coating was very close to the value reported for the strongest-to-date protein-based underwater adhesive (underwater adhesion energy). This huge difference in adhesion underscores the powerful contribution of the LLPS-driven process in promoting both the initial priming and wetting of a substrate and the subsequent self-assembly of the locally concentrated MTLC monomers into extremely dense and highly uniform amyloid nanofibers.

Note that the MTLC fusion monomers also contain a marine mussel adhesive plaque protein, we next assessed how the presence of the mfp5 fusion domain influenced the adhesion of three different coatings by coating mica at low temperature with TDP-43 LC domain only, unmodified MTLC, or tyrosinase-modified MTLC bearing DOPA residues. Even lacking tyrosinase treatment, the presence of the mfp5 fusion domain substantially increased the adhesive strength of the coating: the adhesion of the unmodified MTFP coating was 1.6 times stronger than the coating made from the TDP-43 LC domain alone. Impressively, the in vitro conversion of the tyrosine residues on the MTLC monomers into DOPA residues via tyrosinase treatment increased the adhesion strength of the amyloid nanofiber coating by more than 2.7 times, making it by far the strongest ever reported protein-based underwater adhesive (with underwater adhesion energy approaching 48.1 mJ m$^{-2}$) (FIG. 3C). Beyond their contribution to increasing adhesion, it was also clear that the DOPA residues on the mfp5 fusion domains enhanced intramolecular interactions and absorption on the gold substrate during LLPS-mediated deposition: QCM-D analysis showed that the tyrosine-modified MTLC coatings were even denser than the unmodified MTLC coatings (FIG. 3D).

There is an important distinction between LC domain-driven LLPS and another LLPS mechanism—coacervation—that is used by sandcastle worms for priming and wetting and that has inspired existing biomimetic adhesives. Formation of coacervate structures is electrostatically-driven, and is thus dependent on pH, and engineered charge-charge-based coaceravates are therefore currently limited to applications in narrow pH ranges. Given that it is likely the α-helix and aromatic residues in the LC-domain that provide the hydrophobic force to drive the LLPS that we observed during low-temperature MTLC coating deposition, we speculated that LC domain-based LLPS may enable coating applications over a wide range of pH values. Indeed, MTLC coatings on mica could were deposited from solutions at a wide range of pH values (3-11) at 4° C., all of which exceeded the adhesion performance of any previously reported protein-based underwater adhesives (FIG. 3E).

We next undertook the challenge of applying MTLC coatings to polytetrafluoroethylene (PTFE, "Teflon"), which is an extraordinarily "nonstick" substance. Following incubation of flat Teflon wafers overnight at 4° C., comparison of UV light (254 nm) images revealed the successful deposition of a thick MTLC coating on the Teflon, and water contact angle analysis demonstrated that this coating significantly and dramatically decreased the contact angle of the hydrophobic PTFE surface, from 108.4°±1.4° to 68.7°±2.1° (FIG. 4A). When we incubated uncoated and MTLC-coated PTFE wafers with CdSeS@ZnS quantum dots (QDs), which can interact with the MTLC molecules via His-tag affinity, we observed QDs adsorbed uniformly on the surface of the coated Teflon wafers but found that almost no QDs were present on uncoated Teflon. Cross section images of the MTLC coating by SEM revealed that the surface of the wafer had a thick and uniform coating (FIG. 4B). XPS spectral analysis revealed that, compared to uncoated PTFE, PTFE, wafers coated with MTLC amyloid nanofibers had almost no signal for Fluorine (F1s) but had significant signals for Oxygen (O1s) and Nitrogen (N1s) from the protein coating layers. We also found that coated wafers had decreased signals for Carbon (C1s) arising from C—F bonds, but had increased signals for Carbon (C1s) arising from C—O, C—N, and C—C bonds.

Exploiting the ability of our LLPS-driven MTLC process to coat difficult-to-access surfaces, we also conducted proof-of-concept demonstrations for the coating of difficult-to-access interior surfaces including the interior surfaces of a flexible Teflon pipe (FIG. 4C) and the channel of a microfluidic device (FIG. 4D). Again, the ability of the MTLC coatings to adsorb QDs allowed us to post-treat and thus visualize MTLC coatings on these and other challenging substrates (e.g., highly flexible polyethylene terephthalate ("Mylar") thin films) (FIG. S22); the successful formation of thick and uniform MTLC coatings on each of these materials underscored that our LLPS-driven technique can be used to coat a great diversity of surfaces.

To further explore practical applications of our LLPS-driven MTLC adhesives, we turned to utilize these materials as underwater glues for repairing damages by co-injecting purified MTLC monomers in solution with non-sticky polystyrene (PS) micro-spheres into a damaged site scratched onto a PTEF substrate (FIG. 4E). Upon incubation at 4° C. for 12 hours, an LLPS-driven MTLC coating formed on the surface of the damage site and on the surface of the micro-spheres; the coating functioned as a glue to aggregate the micro-spheres to each other and to the substrate surface, thereby retaining them in place and filling the damage site. Both fluorescent and SEM images showed that the micro-spheres specifically accumulate in the damage site, clearly demonstrating the utility of the LLPS-driven coating for damage repair.

EXAMPLES

We demonstrated functionality with representative MAP-LC dimeric protein combinations. We demonstrated that FUS LC, GFP-FUS LC, GFP-FUS LC-mfp5 all possess property of reversible, liquid-liquid phase separation, and GFP-FUS LC-mfp5 shows underwater adhesion while displaying green fluorescence. We demonstrated that mfp5-FUS LC, mfp3-TDP-43 LC, and mCherry-FUS LC-mfp3 were also constructed, and mCherry-FUS LC-mfp3 possess underwater adhesion while displaying red fluorescence. We demonstrated that Spytag-FUS and mfp5-spycatcher were constructed separately. When the two proteins were mixed at 1:1 molar ratio, they covalently interact to form conjugated proteins that exhibited underwater adhesion.

MTLC adhesives can be deposited over difficult-to-access interfaces, such as the channels in micro-fluidic devices and the walls of microtubules. FIG. 5 (A) is a schematic illustration showing the fluidic device made of PDMS covered on a glass slide. MTLC were injected into the fluidic device and incubated at 4° C. Then QDs were injected into the fluidic device to assemble on the MTLC coating on inside walls. Then the channel was washed by distilled water. (B) 3D images was taken by a confocal fluorescent microscopy. (C) In situ photograph was taken under UV light. (D) SEM image and (E) SEM sectional image showing the inside walls of channel were coated with protein.

MTLC coatings can serve as universal coatings for diverse substrates. FIGS. 6A-C: (A) Digital images of red ODs assembled on MTLC coated surfaces. (B) 3D image of micro PE tube. Red QDs assembled on MTLC coated inside wall. (C) Water contact angle measurement of various surfaces with/without MTLC coatings. Teflon plate: 108.4°+1.4°, 68.7°+2.1°; PS plate: 88.6°+1.5°, 85.2°+1.0°; cover glass: 58.3°+1.9°, 76.0°+2.5°; Silicon wafer: 48.6°+2.3°, 80.3°+1.3°; Aluminum foil: 53.5°+3.9°, 67.5°+0.9°; Iron sheet: 66.8°+1.6°, 75.3°+1.7°.

Figure 7B:
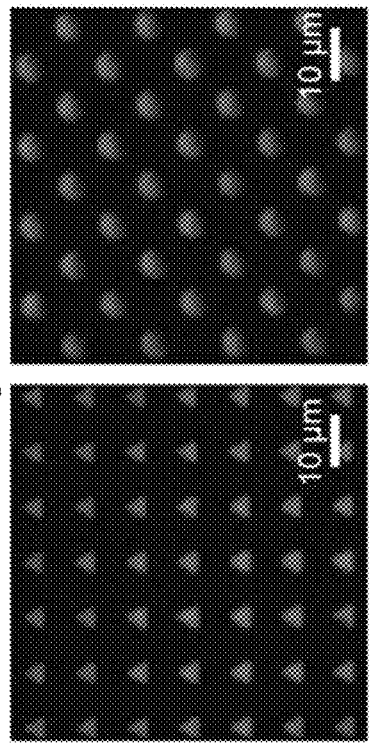
Figure 7A:
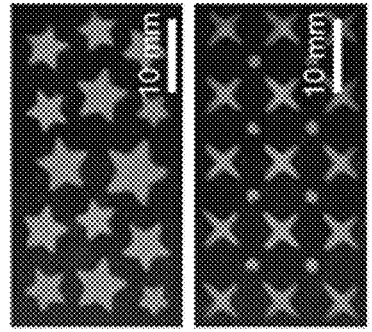

MTLC coatings as patterned arrays for binding specific objects. FIGS. 7A-C: (A) QDs assembled on lithography patterns mediated by specific mask plates. (B) QDs assembled on soft lithography patterns. (C) Micro-scale pattern displays an orderly light spot under green laser which indicates long range ordered pattern achieved.

Figure 8C:
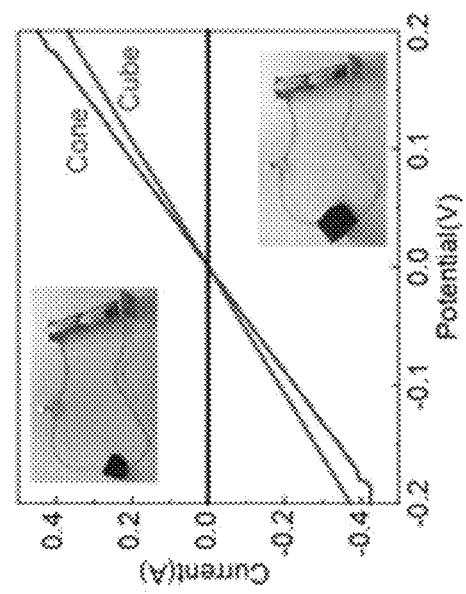
FIGS. 8A-C. (A) Photograph of MTLC coating (left) and copper deposition (right) on the inside wall of PP Eppendorf tube by electro-less metal deposition. (B) Photographs of porous resin models printed by 3D printer before and after copper deposition. (C) C-V curves of copper deposited 3D model. Inserted images are circuit demo of copper deposited 3D model working as an electrical conductor to light the diode.
Figure 8B:
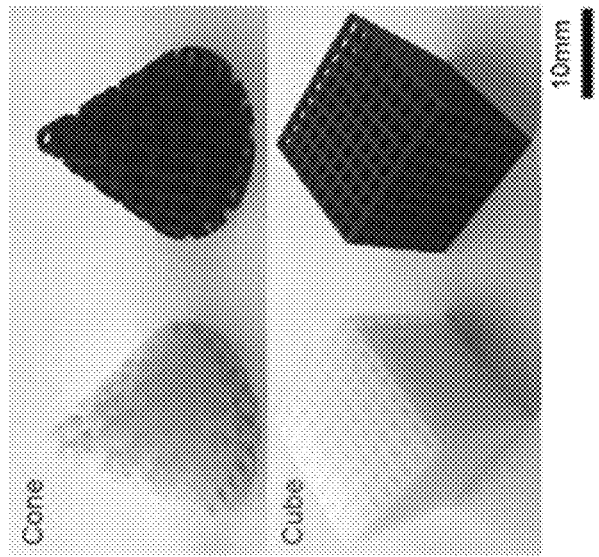
Figure 8A:
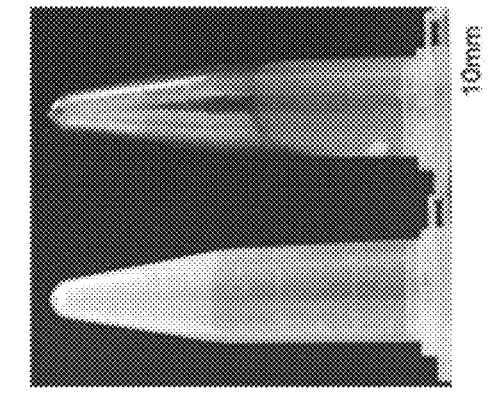

MTLC coatings for electronic devices: deposition of metal layers et al. on challenging surfaces. FIGS. 8A-C: (A) Photograph of MTLC coating (left) and copper deposition (right) on the inside wall of PP Eppendorf tube by electroless metal deposition. (B) Photographs of porous resin models printed by 3D printer before and after copper deposition. (C) C-V curves of copper deposited 3D model. Inserted images are circuit demo of copper deposited 3D model working as an electrical conductor to light the diode.

The invention claimed is:

1. A dimeric protein comprising a marine adhesive protein (MAP) domain and a liquid-liquid phase separation (LLPS) mediating low complexity (LC) domain;
wherein the marine adhesive protein (MAP) is a polypeptide selected from the group consisting of:
a) a mussel foot protein selected from the group consisting of: mfp5, mfp3 and mfp3s;
b) a barnacle adhesive protein selected from the group consisting of: cp19k, cp20k, and cp68k; and
c) a sandcastle worm adhesive protein selected from the group consisting of: Pc2 and Pc3;
wherein the low complexity (LC) domain is a polypeptide selected from the group consisting of:
LC domain TAR DNA-binding protein 43 (TDP-43) with amino acid sequence of (SEQ ID NO: 01)
KHNSNRQLERSGREGGNPGGFGNQGGFGNSRGGGAGLGNNQGSNMGGGM

NFGAFSINPAMMAAAQAALQSSWGMMGMLASQQNQSGPSGNNQNQGNMQ

REPNQAFGSGNNSYSGSNSGAAIGWGSASNAGSGSGFNGGFGSSMDSKS

SGWGM;

heterogeneous nuclear ribonucleoprotein A1 (hnRNPA1) with amino acid sequence of (SEQ ID NO: 03)
MASASSSQRGRSGSGNFGGGRGGGFGGNDNFGRGGNFSGRGGFGGSRGG

GGYGGSGDYNGFGNDSNFGGGGSYNDFGNYNNQSSNFGPMKGGNFGG

RSSGPYGGGGQYFAKPRNQGGYGGSSSSSSYGSGRRF;

heterogeneous nuclear ribonucleoprotein A2 (hnRNPA2) with amino acid sequence of (SEQ ID NO: 04)
MQEVQSSRSGRGGNFGFGDSRGGGGNFGPGPGSNFRGGSDGYGSGRGFG

DGYNGYGGGPGGGNFGGSPGYGGGRGGYGGGGPGYGNQGGGYGGGYDNY

GGGNYGSGNYNDFGNYNQQPSNYGPMKSGNFGGSRNMGGPYGGGNYGPG

GSGGSGGYGGRSRY;

cytotoxic granule-associated RNA binding protein TIA1 with amino acid sequence of (SEQ ID NO: 05)
INPVQQQNQIGYPQPYGQWGQWYGNAQQIGQYMPNGWQVPAYGMYGQAW

NQQGENQTQSSAPWMGPNYGVQPPQGQNGSMLPNQPSGYRVAGYETQ;

cytoplasmic polyadenylation element binding protein 2 (CPEB2) with amino acid sequence of (SEQ ID NO: 06)
PPPSPDSENGFYPGLPSSMNPAFFPSFSPVSPHGCTGLSVPTSGGGGG

FGGPFSATAVPPPPPPAMNIPQQQPPPPAAPQQPQSRRSPVSPQLQQQH

QAAAAAFLQQRNSYNHHQPLLKQSPWSNHQSSGWGTGSM;

fragile X mental retardation protein (FMRP) with amino acid sequence of (SEQ ID NO: 07)
GQGMGRGSRPYRNRGHGRRGPGYTSGTNSEASNASETESDHRDELSDWS

LAPTEEERESFLRRGDGRRRGGGGRGQGGRGRGGGFKGNDDHSRTDNRP

RNPREAKGRTTDGSLQIRVDCNNERSVHTKTLQNTSSEGSRLRTGKDRN

QKKEKPDSVDGQQPLVNGVP;

cold inducible RNA binding protein (CIRBP) with amino acid sequence of (SEQ ID NO: 08)
MASDEGKLFVGGLSFDTNEQSLEQVFSKYGQISEVVVVKDRETQRSRGF

GFVTFENIDDAKDAMMAMNGKSVDGRQIRVDQAGKSSDNRSRGYRGGSA

GGRGFFRGGRGRGRGFSRGGGDRGYGGNRFESRSGGYGGSRDYYSSRSQ

SGGYSDRSSGGSYRDSYDSYATHNE;

RNA binding motif protein 3 (RBM3) with amino acid sequence of (SEQ ID NO: 09)
MSSEEGKLFVGGLNFNTDEQALEDHFSSFGPISEVVVVKDRETQRSRGF

GFITFTNPEHASVAMRAMNGESLDGRQIRVDHAGKSARGTRGGGFGAHG

RGRSYSRGGGDQGYGSGRYYDSRPGGYGYGYGRSRDYNGRNQGGYDRYS

GGNYRDNYDN;

and yeast Sup35 with amino acid sequence of (SEQ ID NO: 10)
SDSNQGNNQQNYQQYSQNGNQQQGNNRYQGYQAYNAQAQPAGGYYQNYQ

GYSGYQQGGYQQYNPDAGYQQQYNPQGGYQQYNPQGGYQQQFNPQGGRG

NYKNFNYNNSLQGYQAGFQPQSQGMSLNDFQKQQKQ.

2. The dimeric protein of claim 1, wherein the low complexity (LC) domain is the LC domain of TAR DNA-binding protein 43 (TDP-43).

3. The dimeric protein of claim 1, wherein the domains are linked in a fusion protein.

4. The dimeric protein of claim 1 wherein the domains are linked through affinity tags on the domains.

5. The dimeric protein of claim 1, wherein the marine adhesive protein (MAP) is the mussel foot protein selected from the group consisting of: mfp5, mfp3 and mfp3s; and the low complexity (LC) domain is the LC domain of TAR DNA-binding protein 43 (TDP-43).

6. An amyloid nanofiber coating comprising the dimeric protein of claim 1.

7. The amyloid nanofiber coating of claim 6, wherein the amyloid nanofiber coating is underwater.

8. An underwater amyloid nanofiber coating comprising the dimeric protein of claim 1, providing underwater adhesion energy at least double that of a coating of a corresponding MAP, and greater than 30 or 40mJ m$^{-2}$.

9. The underwater amyloid nanofiber coating of claim 8, wherein the underwater adhesion energy is 2-3 times of a coating of a corresponding MAP.

10. The underwater amyloid nanofiber coating of claim 8, wherein the underwater adhesion energy is in the range of 30-50 mJ m$^{-2}$.

11. The underwater amyloid nanofiber coating of claim 8, wherein the underwater adhesion energy is in the range of 40-50 mJ m$^{-2}$.

12. The coating of claim 6, micropatterned on a substrate.

13. A substrate comprising the coating of claim 6.

14. The coating of claim 12, wherein the substrate is selected from metal, polymer and inorganic substrates, and flexible and interior surfaces of the substrate is coated with the coating.

15. The coating of claim 14, wherein the flexible and interior surfaces of the substrate are the channels in microfluidic devices and the walls of microtubules.

16. A method of making an amyloid nanofiber coating on a substrate comprising:
  incubating the dimeric protein of claim 1, under conditions wherein a LLPS induced amyloid nanofiber coating comprising the dimeric protein forms on the substrate.

17. The method of claim 16, operable over a range of pH conditions that is pH 3-11.

18. The method of claim 16, wherein the substrate is selected from metal, polymer and inorganic substrates, and flexible and interior surfaces of the substrate is coated with the coating.

19. The method of claim 18, wherein the flexible and interior surfaces of the substrate are the channels in microfluidic devices and the walls of microtubules.

20. The method of claim 16, wherein the coating is micropatterned on the substrate, by mask-assisted patterning or soft lithography.

* * * * *

```
                       SEQUENCE LISTING

<160> NUMBER OF SEQ ID NOS: 10

<210> SEQ ID NO 1
<211> LENGTH: 152
<212> TYPE: PRT
<213> ORGANISM: Homo Sapiens

<400> SEQUENCE: 1

Lys His Asn Ser Asn Arg Gln Leu Glu Arg Ser Gly Arg Phe Gly Gly
1               5                   10                  15

Asn Pro Gly Gly Phe Gly Asn Gln Gly Gly Phe Gly Asn Ser Arg Gly
            20                  25                  30

Gly Gly Ala Gly Leu Gly Asn Asn Gln Gly Ser Asn Met Gly Gly Gly
        35                  40                  45

Met Asn Phe Gly Ala Phe Ser Ile Asn Pro Ala Met Met Ala Ala Ala
    50                  55                  60

Gln Ala Ala Leu Gln Ser Ser Trp Gly Met Met Gly Met Leu Ala Ser
65                  70                  75                  80

Gln Gln Asn Gln Ser Gly Pro Ser Gly Asn Asn Gln Asn Gln Gly Asn
                85                  90                  95

Met Gln Arg Glu Pro Asn Gln Ala Phe Gly Ser Gly Asn Asn Ser Tyr
            100                 105                 110

Ser Gly Ser Asn Ser Gly Ala Ala Ile Gly Trp Gly Ser Ala Ser Asn
        115                 120                 125

Ala Gly Ser Gly Ser Gly Phe Asn Gly Gly Phe Gly Ser Ser Met Asp
    130                 135                 140

Ser Lys Ser Ser Gly Trp Gly Met
145                 150

<210> SEQ ID NO 2
<211> LENGTH: 213
<212> TYPE: PRT
<213> ORGANISM: Homo Sapiens

<400> SEQUENCE: 2

Ala Ser Asn Asp Tyr Thr Gln Gln Ala Thr Gln Ser Tyr Gly Ala Tyr
1               5                   10                  15

Pro Thr Gln Pro Gly Gln Gly Tyr Ser Gln Gln Ser Ser Gln Pro Tyr
```

```
                20                  25                  30
Gly Gln Gln Ser Tyr Ser Gly Tyr Ser Gln Ser Thr Asp Thr Ser Gly
             35                  40                  45

Tyr Gly Gln Ser Ser Tyr Ser Ser Tyr Gly Gln Ser Gln Asn Thr Gly
 50                  55                  60

Tyr Gly Thr Gln Ser Thr Pro Gln Gly Tyr Gly Ser Thr Gly Gly Tyr
 65                  70                  75                  80

Gly Ser Ser Gln Ser Ser Gln Ser Ser Tyr Gln Gln Ser Ser Tyr
                 85                  90                  95

Pro Gly Tyr Gly Gln Gln Pro Ala Pro Ser Ser Thr Ser Gly Ser Tyr
             100                 105                 110

Gly Ser Ser Ser Gln Ser Ser Tyr Gly Gln Pro Gln Ser Gly Ser
                115                 120                 125

Tyr Ser Gln Gln Pro Ser Tyr Gly Gly Gln Gln Ser Tyr Gly Gln
             130                 135                 140

Gln Gln Ser Tyr Asn Pro Pro Gln Gly Tyr Gly Gln Gln Asn Gln Tyr
145                 150                 155                 160

Asn Ser Ser Ser Gly Gly Gly Gly Gly Gly Gly Gly Gly Asn Tyr
                165                 170                 175

Gly Gln Asp Gln Ser Ser Met Ser Ser Gly Gly Ser Gly Gly Gly
             180                 185                 190

Tyr Gly Asn Gln Asp Gln Ser Gly Gly Gly Ser Gly Gly Tyr Gly
             195                 200                 205

Gln Gln Asp Arg Gly
         210

<210> SEQ ID NO 3
<211> LENGTH: 135
<212> TYPE: PRT
<213> ORGANISM: Homo Sapiens

<400> SEQUENCE: 3

Met Ala Ser Ala Ser Ser Ser Gln Arg Gly Arg Ser Gly Ser Gly Asn
1               5                  10                  15

Phe Gly Gly Gly Arg Gly Gly Phe Gly Gly Asn Asp Asn Phe Gly
             20                  25                  30

Arg Gly Gly Asn Phe Ser Gly Arg Gly Gly Phe Gly Gly Ser Arg Gly
             35                  40                  45

Gly Gly Gly Tyr Gly Gly Ser Gly Asp Gly Tyr Asn Gly Phe Gly Asn
 50                  55                  60

Asp Gly Ser Asn Phe Gly Gly Gly Gly Ser Tyr Asn Asp Phe Gly Asn
 65                  70                  75                  80

Tyr Asn Asn Gln Ser Ser Asn Phe Gly Pro Met Lys Gly Gly Asn Phe
                 85                  90                  95

Gly Gly Arg Ser Ser Gly Pro Tyr Gly Gly Gly Gly Gln Tyr Phe Ala
             100                 105                 110

Lys Pro Arg Asn Gln Gly Gly Tyr Gly Gly Ser Ser Ser Ser Ser Ser
             115                 120                 125

Tyr Gly Ser Gly Arg Arg Phe
             130                 135

<210> SEQ ID NO 4
<211> LENGTH: 161
<212> TYPE: PRT
<213> ORGANISM: Homo Sapiens
```

```
<400> SEQUENCE: 4

Met Gln Glu Val Gln Ser Ser Arg Ser Arg Gly Gly Asn Phe Gly
1               5                   10                  15

Phe Gly Asp Ser Arg Gly Gly Gly Asn Phe Gly Pro Gly Pro Gly
                20                  25                  30

Ser Asn Phe Arg Gly Gly Ser Asp Gly Tyr Gly Ser Arg Gly Phe
            35                  40                  45

Gly Asp Gly Tyr Asn Gly Tyr Gly Gly Pro Gly Gly Asn Gly Phe
        50                  55                  60

Gly Gly Ser Pro Gly Tyr Gly Gly Arg Gly Gly Tyr Gly Gly Gly
65                  70                  75                  80

Gly Pro Gly Tyr Gly Asn Gln Gly Gly Gly Tyr Gly Gly Tyr Asp
                85                  90                  95

Asn Tyr Gly Gly Gly Asn Tyr Gly Ser Gly Asn Tyr Asn Asp Phe Gly
                100                 105                 110

Asn Tyr Asn Gln Gln Pro Ser Asn Tyr Gly Pro Met Lys Ser Gly Asn
                115                 120                 125

Phe Gly Gly Ser Arg Asn Met Gly Gly Pro Tyr Gly Gly Asn Tyr
                130                 135                 140

Gly Pro Gly Gly Ser Gly Gly Ser Gly Gly Tyr Gly Gly Arg Ser Arg
145                 150                 155                 160

Tyr

<210> SEQ ID NO 5
<211> LENGTH: 96
<212> TYPE: PRT
<213> ORGANISM: Homo Sapiens

<400> SEQUENCE: 5

Ile Asn Pro Val Gln Gln Asn Gln Ile Gly Tyr Pro Gln Pro Tyr
1               5                   10                  15

Gly Gln Trp Gly Gln Trp Tyr Gly Asn Ala Gln Gln Ile Gly Gln Tyr
                20                  25                  30

Met Pro Asn Gly Trp Gln Val Pro Ala Tyr Gly Met Tyr Gly Gln Ala
            35                  40                  45

Trp Asn Gln Gln Gly Phe Asn Gln Thr Gln Ser Ser Ala Pro Trp Met
        50                  55                  60

Gly Pro Asn Tyr Gly Val Gln Pro Pro Gln Gly Gln Asn Gly Ser Met
65                  70                  75                  80

Leu Pro Asn Gln Pro Ser Gly Tyr Arg Val Ala Gly Tyr Glu Thr Gln
                85                  90                  95

<210> SEQ ID NO 6
<211> LENGTH: 137
<212> TYPE: PRT
<213> ORGANISM: Homo Sapiens

<400> SEQUENCE: 6

Pro Pro Pro Ser Pro Asp Ser Glu Asn Gly Phe Tyr Pro Gly Leu Pro
1               5                   10                  15

Ser Ser Met Asn Pro Ala Phe Phe Pro Ser Ser Val Ser Pro
            20                  25                  30

His Gly Cys Thr Gly Leu Ser Val Pro Thr Ser Gly Gly Gly Gly
            35                  40                  45

Gly Phe Gly Gly Pro Phe Ser Ala Thr Ala Val Pro Pro Pro Pro
50                  55                  60
```

```
Pro Ala Met Asn Ile Pro Gln Gln Gln Pro Pro Pro Ala Ala Pro
 65                  70                  75                  80

Gln Gln Pro Gln Ser Arg Arg Ser Pro Val Ser Pro Gln Leu Gln Gln
                 85                  90                  95

Gln His Gln Ala Ala Ala Ala Phe Leu Gln Gln Arg Asn Ser Tyr
            100                 105                 110

Asn His His Gln Pro Leu Leu Lys Gln Ser Pro Trp Ser Asn His Gln
            115                 120                 125

Ser Ser Gly Trp Gly Thr Gly Ser Met
        130                 135
```

<210> SEQ ID NO 7
<211> LENGTH: 167
<212> TYPE: PRT
<213> ORGANISM: Homo Sapiens

<400> SEQUENCE: 7

```
Gly Gln Gly Met Gly Arg Gly Ser Arg Pro Tyr Arg Asn Arg Gly His
  1               5                  10                  15

Gly Arg Arg Gly Pro Gly Tyr Thr Ser Gly Thr Asn Ser Glu Ala Ser
                 20                  25                  30

Asn Ala Ser Glu Thr Glu Ser Asp His Arg Asp Glu Leu Ser Asp Trp
             35                  40                  45

Ser Leu Ala Pro Thr Glu Glu Arg Glu Ser Phe Leu Arg Arg Gly
 50                  55                  60

Asp Gly Arg Arg Gly Gly Gly Arg Gly Gln Gly Gly Arg Gly
 65                  70                  75                  80

Arg Gly Gly Gly Phe Lys Gly Asn Asp Asp His Ser Arg Thr Asp Asn
                 85                  90                  95

Arg Pro Arg Asn Pro Arg Glu Ala Lys Gly Arg Thr Thr Asp Gly Ser
             100                 105                 110

Leu Gln Ile Arg Val Asp Cys Asn Asn Glu Arg Ser Val His Thr Lys
            115                 120                 125

Thr Leu Gln Asn Thr Ser Ser Glu Gly Ser Arg Leu Arg Thr Gly Lys
130                 135                 140

Asp Arg Asn Gln Lys Lys Glu Lys Pro Asp Ser Val Asp Gly Gln Gln
145                 150                 155                 160

Pro Leu Val Asn Gly Val Pro
                165
```

<210> SEQ ID NO 8
<211> LENGTH: 172
<212> TYPE: PRT
<213> ORGANISM: Homo Sapiens

<400> SEQUENCE: 8

```
Met Ala Ser Asp Glu Gly Lys Leu Phe Val Gly Gly Leu Ser Phe Asp
  1               5                  10                  15

Thr Asn Glu Gln Ser Leu Glu Gln Val Phe Ser Lys Tyr Gly Gln Ile
                 20                  25                  30

Ser Glu Val Val Val Val Lys Asp Arg Glu Thr Gln Arg Ser Arg Gly
             35                  40                  45

Phe Gly Phe Val Thr Phe Glu Asn Ile Asp Asp Ala Lys Asp Ala Met
 50                  55                  60

Met Ala Met Asn Gly Lys Ser Val Asp Gly Arg Gln Ile Arg Val Asp
 65                  70                  75                  80
```

Gln Ala Gly Lys Ser Ser Asp Asn Arg Ser Arg Gly Tyr Arg Gly Gly
                85                  90                  95

Ser Ala Gly Gly Arg Gly Phe Phe Arg Gly Gly Arg Gly Arg Gly Arg
            100                 105                 110

Gly Phe Ser Arg Gly Gly Asp Arg Gly Tyr Gly Gly Asn Arg Phe
        115                 120                 125

Glu Ser Arg Ser Gly Gly Tyr Gly Gly Ser Arg Asp Tyr Tyr Ser Ser
130                 135                 140

Arg Ser Gln Ser Gly Gly Tyr Ser Asp Arg Ser Ser Gly Gly Ser Tyr
145                 150                 155                 160

Arg Asp Ser Tyr Asp Ser Tyr Ala Thr His Asn Glu
                165                 170

<210> SEQ ID NO 9
<211> LENGTH: 157
<212> TYPE: PRT
<213> ORGANISM: Homo Sapiens

<400> SEQUENCE: 9

Met Ser Ser Glu Glu Gly Lys Leu Phe Val Gly Gly Leu Asn Phe Asn
1               5                   10                  15

Thr Asp Glu Gln Ala Leu Glu Asp His Phe Ser Ser Phe Gly Pro Ile
                20                  25                  30

Ser Glu Val Val Val Lys Asp Arg Glu Thr Gln Arg Ser Arg Gly
            35                  40                  45

Phe Gly Phe Ile Thr Phe Thr Asn Pro Glu His Ala Ser Val Ala Met
    50                  55                  60

Arg Ala Met Asn Gly Glu Ser Leu Asp Gly Arg Gln Ile Arg Val Asp
65                  70                  75                  80

His Ala Gly Lys Ser Ala Arg Gly Thr Arg Gly Gly Phe Gly Ala
                85                  90                  95

His Gly Arg Gly Arg Ser Tyr Ser Arg Gly Gly Asp Gln Gly Tyr
            100                 105                 110

Gly Ser Gly Arg Tyr Tyr Asp Ser Arg Pro Gly Gly Tyr Gly Tyr
        115                 120                 125

Tyr Gly Arg Ser Arg Asp Tyr Asn Gly Arg Asn Gln Gly Gly Tyr Asp
130                 135                 140

Arg Tyr Ser Gly Gly Asn Tyr Arg Asp Asn Tyr Asp Asn
145                 150                 155

<210> SEQ ID NO 10
<211> LENGTH: 134
<212> TYPE: PRT
<213> ORGANISM: Homo Sapiens

<400> SEQUENCE: 10

Ser Asp Ser Asn Gln Gly Asn Asn Gln Gln Asn Tyr Gln Gln Tyr Ser
1               5                   10                  15

Gln Asn Gly Asn Gln Gln Gly Asn Asn Arg Tyr Gln Gly Tyr Gln
            20                  25                  30

Ala Tyr Asn Ala Gln Ala Gln Pro Ala Gly Gly Tyr Tyr Gln Asn Tyr
    35                  40                  45

Gln Gly Tyr Ser Gly Tyr Gln Gln Gly Gly Tyr Gln Gln Tyr Asn Pro
    50                  55                  60

Asp Ala Gly Tyr Gln Gln Gln Tyr Asn Pro Gln Gly Gly Tyr Gln Gln
65                  70                  75                  80

Tyr Asn Pro Gln Gly Gly Tyr Gln Gln Gln Phe Asn Pro Gln Gly Gly
                    85                  90                  95

Arg Gly Asn Tyr Lys Asn Phe Asn Tyr Asn Asn Ser Leu Gln Gly Tyr
                100                 105                 110

Gln Ala Gly Phe Gln Pro Gln Ser Gln Gly Met Ser Leu Asn Asp Phe
            115                 120                 125

Gln Lys Gln Gln Lys Gln
        130